United States Patent [19]

Gries et al.

[11] Patent Number: 4,647,447

[45] Date of Patent: Mar. 3, 1987

[54] DIAGNOSTIC MEDIA

[75] Inventors: Heinz Gries; Douwe Rosenberg; Hanns-Joachim Weinmann, all of Berlin, Fed. Rep. of Germany

[73] Assignee: Schering Aktiengesellschaft, Berlin and Bergkamen, Fed. Rep. of Germany

[21] Appl. No.: 573,184

[22] Filed: Jan. 23, 1984

Related U.S. Application Data

[63] Continuation-in-part of Ser. No. 401,594, Jul. 26, 1982, abandoned.

[30] Foreign Application Priority Data

Jul. 24, 1981 [DE] Fed. Rep. of Germany ....... 3129906
Jan. 21, 1983 [DE] Fed. Rep. of Germany ....... 3302410

[51] Int. Cl.$^4$ .................... A61K 49/00; C07C 101/26; C07F 9/38; G01N 24/02
[52] U.S. Cl. ........................................ 424/9; 424/2; 424/4
[58] Field of Search .................... 424/2, 4, 9; 536/173

[56] References Cited

U.S. PATENT DOCUMENTS

| | | | |
|---|---|---|---|
| 4,125,599 | 11/1978 | Wiegert | 260/515 A |
| 4,167,564 | 9/1979 | Jensen | 424/177 |
| 4,206,132 | 6/1980 | Sievers | 436/173 X |
| 4,478,816 | 10/1984 | Ledley et al. | 424/4 |

FOREIGN PATENT DOCUMENTS

| | | |
|---|---|---|
| 0055028 | 6/1982 | European Pat. Off. |
| 0063946 | 11/1982 | European Pat. Off. |
| 0065347 | 11/1982 | European Pat. Off. |
| 2527158 | 12/1976 | Fed. Rep. of Germany |
| 2918842 | 12/1979 | Fed. Rep. of Germany |
| 1111504 | 3/1956 | France |
| 484M | 5/1961 | France |
| 988M | 12/1961 | France |
| 1273446 | 5/1972 | United Kingdom |
| 1366352 | 9/1974 | United Kingdom |
| 1398276 | 6/1975 | United Kingdom |
| 1399368 | 7/1975 | United Kingdom |
| 1405372 | 9/1975 | United Kingdom |
| 1435967 | 5/1976 | United Kingdom |
| 1466969 | 3/1977 | United Kingdom |
| 1497904 | 1/1978 | United Kingdom |
| 1504243 | 3/1978 | United Kingdom |
| 1522103 | 8/1978 | United Kingdom |
| 1525418 | 9/1978 | United Kingdom |
| 2001969A | 2/1979 | United Kingdom |
| 2008944 | 6/1979 | United Kingdom |
| 2019397A | 10/1979 | United Kingdom |
| 1565186 | 4/1980 | United Kingdom |
| 1584787 | 2/1981 | United Kingdom |
| 1594109 | 7/1981 | United Kingdom |
| 1598610 | 9/1981 | United Kingdom |
| 1599256 | 9/1981 | United Kingdom |

OTHER PUBLICATIONS

Chem. Abstracts 91:133246k (1979).
Chemical Abstracts 87:1879b 1977, Chemical Abstracts 93:31813s, 1980, Chemical Abstracts 93:81186k, 1980, Chemical Abstracts 96:115204u, 1982, Chemical Abstracts 95:38681x, 1981.
Article 115 of EPC filing paper (12-4-84).
G. Levy et al, "Paramagnetic Relaxation Agents . . .", Journal of the American Chemical Society, 96, 678-681 (1974).
P. C. Lauterbur et al, "Augmentation of Tissue Water Proton Spin-Lattice Relaxation Rates by In Vivo Addition of Paramagnetic Ions", Frontiers of Biological Energetics, vol. I, 752-759, (Encl. 2).
Bertinchamps, A. J., et al, "Interdependence of Routes Excreting Manganese", Am. J. Phsiol., 211 (i):217-224, 1966.
Cotzias, George C., "Manganese Versus Magnesium: Why are They So Similar In Vitro and So Different In Vivo?", Brookhaven National Laboratory, Upton, L. I., New York, pp. 98-103.
Davies, J. T., "The Clinical Significance of the Essential Biological Metals Codon 1572", Chapter IV—Manganese, pp. 69-80.
Doyle, F. H., et al., "Relaxation Rate Enhancement Observed In Vivo by NMR Imaging", Proceedings of NMR Imaging Symposium held in Nashville, Tenn., on Oct. 26-27, 1980, and abstracted on Journal of Computer Assisted Tomography 5 (2) 295-296.
Dwek, R. A., "Proton Relaxation Enhancement Probes", Advances in Molecular Relaxation Processes, 4(1972) 1-53, Elsevier Pub. Co., Amsterdam.
Eisinger, J., et al., "Transition Metal Binding in DNA Solutions", The Journal of Chemical Physics, vol. 36, No. 7, Apr. 1, 1962, pp. 1721-1729.
Forsberg, John H., "Sc, Y, La—Lu Rare Earth Elements—Part D 1", Gmelin Handbuch der Anorganischen Chemie, 8th ed., Springer-Verlag, New York, 1980, pp. 198-204.
Hosain, F., et al., "Ytterbium—169 Diethylenetriaminepentaacetic Acid Complex—A New Radiopharmaceutical for Brain Scanning", Radiology 91, 1199-1203, 1968.
Lauterbur, P. C., "Progress in NMR Zeugmatographic Imaging", Phil. Trans. R. Soc. Lond. B 289, 483-87 (1980).
Morgan, I. O., et al., "Proton Spin Relaxation in Aqueous Solutions of Paramagnetic Ions . . .", The Journal of Chemical Physics, vol. 31, No. 2, Aug. 1959, pp. 365-368.

List Continued on next page.

Primary Examiner—Richard L. Raymond
Attorney, Agent, or Firm—Millen & White

[57] ABSTRACT

A diagnostic medium contains at least one physiologically well tolerated complex salt comprising an anion of a complexing acid and one or more central ion or ions of an element with an atomic number of 21 to 29, 42, 44 or 57 to 83 and, optionally, one or more physiologically biocompatible cation or cations of an inorganic and/or organic base or amino acid, optionally, with additives customary in galenic formulations, dissolved or suspended in an aqueous medium.

68 Claims, No Drawings

OTHER PUBLICATIONS

Pykett, Ian L., "Nuclear Magnetic Resonance, or NMR, Can Reveal the Distribution of Atoms in a Sample of Material. It Can Do the Same in the Body, Generating Images of Internal Structure without the Use of X Rays", *NMR Imaging in Medicine*, pp. 78–88.

Rote Liste 1977/78.

Weinmann, H. J., et al., "Characteristics of Gadoilnium–DTPA Complex. A Potential NMR Contrast Agent", in AJR 142, 619–624 (1984).

Brady et al, Radiology, 144, 343 (1982).

Young et al., J. Comput. Tomography 5,6:543–46 (1981).

Brash et al, AJR, 142:625–630, Mar. 1984.

Carr et al, The Lancet, Mar. 3, 1984, 484–486.

Mendonca-Dias et al, "Paramagnetic Contrast Agents in Nuclear Magnetic Resonance Medical Imaging", Seminars in Nuclear Medicine, vol. XIII, No. 4 (Oct., 1983) pp. 364–376.

Tyler et al, Ultrasonic Imaging 3, 323–329 (1981).

James J. Dechter & George C. Levy, "Aqueous Relaxation Reagents in Nitrogen—15 NMR", Journal of Magnetic Resonance 39, pp. 207–215 (1980).

Dennis R. Burton et al, Progress in NMR Spectroscopie, vol. 13, pp. 1–45: Proton Relaxation Enhancement (PRE) in Biochemistry: A Critical Survey.

Derwent Publications, Abstracts Nos.: 29038 D/16 (4-2-81); 61698V/35 (6-22-74); 07413X/04 (1-13-76); 78609B/43 (1-30-79); 8497X/46 (10-29-76); 81534B/45 (9-29-79); 23893B/12 (3-13-79); 02446 D/03 (1-7-81); 05092C/03 (1-1-80); 34726 D/20 (5-6-81);150/429 (1979); 221/170 (1977); 124/026 (1981); 135A/020 (1975); and 144/005 (1979).

"Probleme der Chelat-Therapie," A. Catsch, *Naturwissenschaften* (1968), pp. 473–477.

Elgavish et al, Journal of the American Chemical Society, 99:6, Mar. 16, 1977, pp. 1762–1765.

Ovitt et al, Improved Instrumentation Etc., NTIS No. PB82-118688, Sep. 1, 1979.

Ovitt et al, Improved Instrumentation Etc., NTIS No. PB 272 617, May, 1977.

Ovitt et al, Improved Instrumentation Etc., NTIS No. PB 268 277, Apr., 1976.

DIAGNOSTIC MEDIA

CROSS-REFERENCE TO RELATED APPLICATIONS

This application is a continuation-in-part of U.S. Ser. No. 401,594, filed on July 26, 1982, now abandoned, and is related to FRG application No. 3,302,410.3 of Jan. 21, 1983, both of whose disclosures are entirely incorporated by reference herein.

BACKGROUND OF THE INVENTION

Complexes or their salts have long been used in medicine, for example, as aids in administering poorly soluble ions (e.g., iron) and as antidotes (in which calcium or zinc complexes are preferred) for detoxification in cases of inadvertent bodily incorporation of heavy metals or their radio isotopes.

SUMMARY OF THE INVENTION

It is an object of this invention to provide complex salts for use in valuable diagnostic techniques.

Upon further study of the specification and appended claims, further objects and advantages of this invention will become apparent to those skilled in the art.

It has now been found that physiologically well tolerated complex salts formed from the anion of a complexing acid and one or more central ions of an element with an atomic number of 21 to 29, 42, 44 or 57 to 83 and, optionally, also formed from one or more physiologically biocompatible cations of an inorganic and/or organic base or amino acid, surprisingly are suitable for producing diagnostic media which are suitable for use in NMR, X-ray and/or ultrasonic diagnosis.

Thus, these objects have been attained by providing, preferably, a diagnostic medium containing at least one physiologically well tolerated complex salt of the formulae I or II

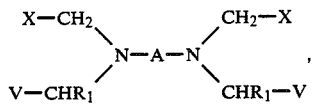
(I)

or $N(CH_2X)_3$      (II), wherein, X is —COOY, —PO$_3$HY or —CONHOY; Y is a hydrogen atom, a metal ion equivalent and/or a physiologically biocompatible cation of an inorganic or organic base or amino acid, A is —CHR$_2$—CHR$_3$—,
—CH$_2$—CH$_2$(ZCH$_2$—CH$_2$)$_m$—,

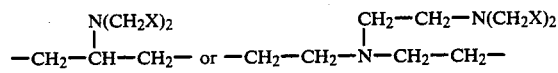

wherein X is defined as above, each R$_1$ is hydrogen or methyl, R$_2$ and R$_3$ together represent a trimethylene group or a tetramethylene group or individually are hydrogen atoms, lower alkyl groups (e.g., 1-8 carbon atoms), phenyl groups, benzyl groups, or R$_2$ is a hydrogen atom and R$_3$ is —(CH$_2$)$_p$—C$_6$H$_4$—W—protein wherein p is 0 or 1, W is —NN—, —NHCOCH$_2$— or —NHCS—, —protein represents a protein residue, m is the number 1, 2 or 3, Z is an oxygen atom or a sulfur atom or the group >NCH$_2$X, or >NCH$_2$CH$_2$OR wherein X is as defined above and R$_4$ is a lower alkyl group (e.g., 1-8 carbon atoms), V has the same meaning as X, or is —CH$_2$OH, —CONH(CH$_2$)$_n$X, or —COB wherein X is as defined above, B is a protein or lipid residue, n is a number from 1 to 12, or if R$_1$, R$_2$ and R$_3$ are hydrogen atoms, both V's together are the group

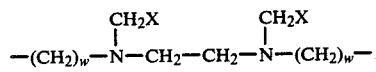

wherein X is as defined above, w is the number 1, 2 or 3, provided that at least two of the substituents Y represent metal ion equivalents of an element with an atomic number of 21 to 29, 42, 44 or 57 to 83.

New such salts include complex salts of the formula

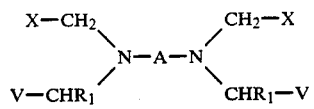

wherein X, A, V and R$_1$ are as defined above provided they contain 3 to 12 substituents Y, of which at least two are a metal ion equivalent of an element with an atomic number of 21 to 29, 42, 44 or 57 to 83 and, in addition, at least one substituent Y is the physiologically biocompatible cation of an organic base or amino acid, wherein the optionally remaining substituents Y represent hydrogen atoms or cations of an inorganic base.

DETAILED DISCUSSION

The element of the above-mentioned atomic number which forms the central ion or ions of the physiologically well tolerated complex salt, obviously must not be radioactive for the intended use of the diagnostic medium according to this invention.

If the medium according to the invention is intended to be used in NMR diagnosis (see, e.g., European patent application 71 564 as well as parent Ser. No. 401,594, both of which are entirely incorporated by reference herein), the central ion of the complex salt must be paramagnetic. It preferably is the divalent or trivalent ions of elements with an atomic number of 21 to 29, 42, 44 and 58 to 70. Suitable ions, for example, include chromium(III), manganese(II), iron(III), iron(II), cobalt(II), nickel(II), copper(II), praseodymium(III), neodymium(III), samarium(III) and ytterbium(III). Because of their very strong magnetic moments, gadolinium(III), terbium(III), dysprosium(III), holmium(III), and erbium(III) are preferred.

If the medium according to the invention is intended for use in X-ray diagnosis, the central ion has to be derived from an element with a higher atomic number to achieve a sufficient absorption of X-rays. It has been found that diagnostic media containing a physiologically well tolerated complex salt with central ions of elements with atomic numbers of 57 to 83 are suitable for this purpose. These include, for example, lanthanum(III), the above mentioned ions of the lanthanide group, gold(III), lead(II) or, especially, bismuth(III).

All of the media according to the invention, also intended for use both in NMR and X-ray diagnosis, are also suitable for use in ultrasonic diagnosis.

By "complexing acid" herein is meant an acid which acts as a ligand for the metals of interest thereby forming a chelate therewith.

Suitable complexing acids include those which are customarily used for complexing of the above mentioned central ions. These include, for example, those containing 3 to 12, preferably 3 to 8, methylene phosphonic acid groups, methylene carbohydroxamic acid groups, carboxyethylidene groups, or especially carboxymethylene groups, one, two or three of which are bonded to a nitrogen atom supporting the complexing. If three of the acid groups are bonded to a nitrogen atom, then the underlying acids complexing the complex salts of formula II are present. If only one or two of the acid groups are bonded to a nitrogen atom, that nitrogen is bonded to another nitrogen atom by an optionally substituted ethylene group or by up to four separate ethylene units separated by a nitrogen or oxygen or sulfur atom supporting the complexing. Complexing acids of this type are preferably those of formula I.

The complexing acids can be coupled as conjugates with biomolecules that are known to concentrate in the organ or part of the organ to be examined. These biomolecules include, for example, hormones such as insulin, prostaglandins, steroid hormones, amino sugars, peptides, proteins, lipids etc. Conjugates with albumins, such as human serum albumin, antibodies, for example, monoclonal antibodies specific to tumor associated antigens, or antimyosin etc. are especially notable. The diagnostic media formed therefrom are suitable, for example, for use in tumor and infarct diagnosis. Conjugates with liposomes, or by inclusion of the salts in liposomes, in both cases which, for example, are used as unilamellar or multilamellar phosphatidylcholine-cholesterol vesicles, are suitable for liver examinations. Conjugating can be conventionally effected either via a carboxyl group of the complexing acid or, in the case of proteins or peptides, also by a $(CH_2)_p$—$C_6H_4$—W—group, as defined for $R_3$ above. Several acid radicals can be partially bonded to the macromolecular biomolecule in the conjugation of the complex salts with proteins, peptides or lipids. In this case, each complexing acid radical can carry a central ion. If the complexing acids are not bonded to biomolecules, they optionally carry two central ions, usually and especially one central ion.

Suitable complex salts of formula I include, for example, those of formula Ia

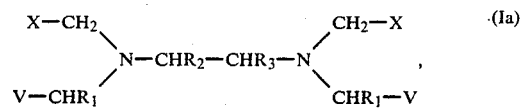

where X, V, $R_1$, $R_2$ and $R_3$ are as defined above.

The following complexing acids, among others, are suitable for production of the complex salts of formula Ia: ethylenediaminetetraacetic acid, ethylenediaminetetraacethydroxamic acid, trans-1, 2-cyclohexenediaminetetraacetic acid, dl-2,3-butylenediamine tetraacetic acid, dl-1,2-butylenediaminetetraacetic acid, dl-1,2-diaminepropanetetraacetic acid, 1,2-diphenylethylenediaminetetraacetic acid, ethylenedinitrilotetrakis(methane phosphonic acid) and N-(2-hydroxyethyl)-ethylenediaminetriacetic acid.

Other suitable complex salts of formula I include, for example, those of formula Ib

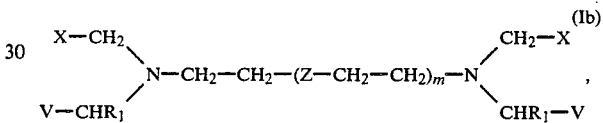

where X, V, Z, $R_1$ and m are as defined above. If Z is an oxygen atom or a sulfur atom, complex salts with m equal to 1 or 2 are preferred.

The following complexing acids, among others, are suitable for production of the complex salts of formula Ib: diethylenetriaminepentaacetic acid, triethylenetetraaminehexaacetic acid, tetraethylenepentaamineheptaacetic acid, 13,23-dioxo-15,18,21-tris(carboxymethyl)-12,15,18,21,24-pentaazapentatriacontanedioic acid, 3,9-bis-(1-carboxyethyl)-3,6,9-triazaundecanedioic acid, diethylenetriaminepentakis-(methylene phosphonic acid), 1,10-diaza-4,7-dioxadecane-1,1-10,10-tetraacetic acid and, 1,10-diaza-4,7-dithiadecane-1,1,10,10-tetraacetic acid.

Moreover, suitable complex salts of formula I, include those of formula Ic

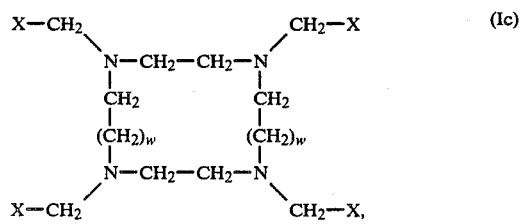

where X and w are as defined above.

The following complexing acids, among others, are suitable for production of the complex salts of formula Ic: 1,4,8,11-tetraazacyclotetradecanetetraacetic acid and especially 1,4,7,10-tetraazacyclododecanetetraacetic acid.

Other complexing acids, which are suitable for production of the complex salts of formula I, include for example: 1,2,3-tris-[bis-(carboxymethyl)-amino-]-propane and nitrilotris-(ethylenenitrilo)-hexaacetic acid. Nitrilotriacetic acid is an example of a complexing acid suitable for production of the complex salts of formula II.

If not all of the hydrogen atoms of the complexing acids are substituted by the central ion or central ions, it is advantageous to increase the solubility of the complex salt to substitute the remaining hydrogen atoms with physiologically biocompatible cations of inorganic and/or organic bases or amino acids. For example, the lithium ion, the potassium ion and especially the sodium ion are suitable inorganic cations. Suitable cations of organic bases include, among others, those of primary, secondary or tertiary amines, for example, ethanolamine, diethanolamine, morpholine, glucamine, N,N-dimethylglucamine or especially N-methylglucamine. Lysines, arginines or ornithines are suitable cations of amino acids, as generally are those of other basic naturally occurring such acids.

All of the complexing acids used in the agents according to the invention are known or can be produced in a way fully conventional in the art. Thus, for example, production of 13,23-dioxo-15,18,21-tris(carboxymethyl)-12,15,18,21,24-pentaazapentatriacontanedioic acid is produced in an improvement of the method proposed by R. A. Bulman et al. in Naturwissenschaften 68 (1981) 483, as follows:

17.85 g (=50 mmole) of 1,5-bis(2,6-dioxomorpholino)-3-azapentane-3-acetic acid is suspended in 400 ml of dry dimethylformamide and heated for 6 hours to 70° C. after addition of 20.13 g (=100 mmole) of 11-aminoundecanoic acid. The clear solution is concentrated in vacuo. The yellow oil residue is stirred with 500 ml of water at room temperature. In this way, a white, voluminous solid precipitates which is suctioned off and washed several times with water. The resulting product is put into 200 ml of acetone for further purification and stirred for 30 minutes at room temperature. After suctioning off and drying in vacuo at 50° C., 36.9 g (=97% of theory) of a white powder with a melting point of 134°–138° C. is obtained.

Conjugation of the complexing acids with biomolecules also occurs by methods fully conventional in the art, for example, by reaction of nucleophilic groups of biomolecules, for example, amino, hydroxy, thio or imidazole groups with an activated derivative of the complexing acid. For example, acid chlorides, acid anhydrides, activated esters, nitrenes or isothiocyanates can be used as activated derivatives of complexing acids. On the other hand, it is also possible conventionally to react an activated biomolecule with the complexing acid. Substituents of the structure —$C_6H_4N_2+$ or $C_6H_4NHCOCH_2$— halogen can also be used for conjugating with proteins.

Production of the complex salts is also known or can be performed fully conventionally as known in the art, e.g., in processes in which the metal oxide or a metal salt (for example, nitrate, chloride or sulfate) of an element with an atomic number of 21 to 29, 42, 44 or 57 to 83 is dissolved or suspended in water and/or a lower alcohol (such as methyl, ethyl or isopropyl alcohol) and added to a solution or suspension of the equivalent amount of the complexing acid in water and/or a lower alcohol and stirred, if necessary, with heating moderately or to the boiling point, until the reaction is completed. If the complex salt that is formed is insoluble in the solvent that is used, it is isolated by filtering. If it is soluble, it can be isolated by evaporation of the solvent to dryness, for example, by spray drying.

If acid groups are still present in the resulting complex salt, it is often advantageous to convert the acidic complex salt into a neutral complex salt by reaction with inorganic and/or organic bases or amino acids, which form physiologically biocompatible cations, and isolate them. In many cases, the procedure is even unavoidable since the dissociation of the complex salt is moved toward neutrality to such an extent by a shift in the pH value during the preparation that only in this way is the isolation of homogeneous products or at least their purification made possible. Production is advantageously performed with organic bases or basic amino acids. It can also be advantageous, however, to perform the neutralization by means of inorganic bases (hydroxides, carbonates or bicarbonates) of sodium, potassium or lithium.

To produce the neutral salts, enough of the desired base can be added to the acid complex salts in an aqueous solution or suspension that the point of neutrality is reached. The resulting solution can then be concentrated to dryness in vacuo. It is often advantageous to precipitate the neutral salts by addition of solvents miscible with water, for example, lower alcohols (methyl, ethyl, isopropyl alcohols, etc.), lower ketones (acetone, etc.), polar ethers (tetrahydrofuran, dioxane, 1,2-dimethoxyethane, etc.) and thus obtain crystallizates that isolate easily and purify well. It has been found particularly advantageous to add the desired bases to the reaction mixture even during complexing and thus eliminate a process stage.

If the acid complex salts contain several free acid groups, it is then often advantageous to produce neutral mixed salts which contain both inorganic and organic physiologically biocompatible cations as counterions. This can be done, for example, by reacting the complexing acids in an aqueous suspension or solution with the oxide or salt of the element supplying the central ion and less than the full amount of an organic base necessary for neutralization, e.g., half, isolating the complex salt that is formed, purifying it, if desired, and then adding it to the amount of inorganic base necessary for complete neutralization. The sequence of adding the bases can also be reversed.

Production of the diagnostic media according to the invention is also performed in a way known in the art. For example, the complex salts, optionally with addition of the additives customary in galenicals, are suspended or dissolved in an aqueous medium and then the solution or suspension is sterilized. Suitable additives include, for example, physiologically biocompatible buffers (as, for example, tromethamine hydrochloride), slight additions of complexing agents (as, for example, diethylenetriaminepentaacetic acid) or, if necessary, electrolytes (for example, sodium chloride).

In principle, it is also possible to produce the diagnostic media according to the invention without isolating the complex salts. In this case, special care must be taken to perform the chelating so that the salts and salt solutions according to the invention are essentially free of uncomplexed, toxically active metal ions. This can be assured, for example, using color indicators such as xylenol orange by control titrations during the production process. The invention therefore also relates to the process for production of the complex compound and its salts. A purification of the isolated complex salt can also be employed as a final safety measure.

If suspensions of the complex salts in water or physiological salt solutions are desired for oral administration or other purposes, a small amount of soluble complex salt is mixed with one or more of the inactive ingredients customary in galenicals and/or surfactants and/or aromatics for flavoring.

The diagnostic media according to this invention preferably contain 1 μmole to 1 mole per liter of the complex salt and, as a rule, are administered in doses of 0.001 to 5 mmole/kg. They are intended for oral and particularly parenteral administration.

The media according to the invention, meet the various requirements for suitability as contrast media for nuclear spin tomography. They are exceptionally suitable for improving the image, e.g., its expressiveness, which is obtained with nuclear spin tomography by enhancement of the signal strength after oral or parenteral application. Moreover, they exhibit the great effectiveness that is necessary to load the body with the least possible amount of foreign substances while achieving beneficial results, and the good tolerance that is necessary to maintain the noninvasive character of the examination. (The compounds mentioned, for example in J. Comput. Tomography 5,6: 543–46 (1981), in Radiology 144, 343 (1982) and in Brevet Special de Medicament No. 484 M(1960) are too toxic). The good aqueous solubility of the media according to the invention makes it possible to produce highly concentrated solutions and in this way to keep the volume load of the circulatory system within supportable limits and compensate for dilution by the body fluids, i.e., NMR diagnostic media must be 100 to 1000 times more soluble in water than for conventional NMR spectroscopy. Moreover, the media according to the invention exhibit not only a great stability in vitro but also an exceptionally great stability in vivo, so that a release or exchange of the ions, which are not covalently bonded in the complexes and which in themselves would be toxic in the 24 hours in which—as pharmacological research has shown—the new contrast media are generaly completely eliminated, occurs only extremely slowly. For example, the conjugates with proteins and antibodies used for tumor diagnosis, even in very low dosage, result in such a surprisingly great enhancement of the signal that in this case solutions in correspondingly low concentrations can be applied.

The media according to the invention are also exceptionally suitable as X-ray contrast media. In this case, it should be particularly stressed that with them no indications of anaphylactic type reactions can be detected as opposed to contrast media containing iodine which are known in biochemical and pharmacological tests. These agents of this invention are especially valuable because of the favorable absorption properties in the range of higher X-ray tube voltages for digital subtraction techniques.

The media according to the invention are also suitable as ultrasonic diagnostic media because of their property of favorably influencing the ultrasonic rate.

In contrast to conventional X-ray diagnosis with radiopaque X-ray contrast media, in NMR diagnosis with paramagnetic contrast medium there is no linear dependence of the signal enhancement on the concentration used. As control tests show, an increase in the applied dosage does not necessarily contribute to a signal enhancement, and with a high dosage of paramagnetic contrast medium the signal can even be obliterated. For this reason, it was surprising that some pathological processes can be seen only after application of a strongly paramagnetic contrast medium, according to the invention, higher than the doses indicated in EP 71564 (which can be from 0.001 mmole/kg to 5 mmole/kg). Thus, for example, a defective blood-brain barrier in the region of a cranial abscess can be detected only after a dose of 0.05–2.5 mmole/kg, preferably 0.1–0.5 mmole/kg, of paramagnetic complex salts of this invention, for example, gadolinium diethylenetriaminepentaacetic acid or manganese-1,2-cyclohexenediaminetetraacetic acid in the form of their salts that have good aqueous solubility. For a dose greater than 0.1 mmole/kg, solutions of high concentrations up to 1 mole/l, preferably 0.25 to 0.75 mole/l, are necessary, since only in this way is the volume load reduced and handling of the injection solution assured.

Particularly low dosages (under 1 mg/kg) and thus lower concentrated solutions (1 μmole/l to 5 mmole/l), than indicated in EP 71564, can be used in this invention for organ-specific NMR diagnosis, for example, for ;detection of tumors and cardiac infarction.

Generally, the agents of this invention are administered in doses of 0.001–5 mmole/kg, preferably 0.005–0.5 mmole/kg for NMR diagnostics; in doses of 0.1–5 mmole/kg, preferably 0.25–1 mmole/kg for X-ray diagnostics, e.g., analogous to meglumine-diatrizoate, and in doses of 0.1–5 mmole/kg, preferably 0.25–1 mmole/kg for ultrasound diagnostics.

Without further elaboration, it is believed that one skilled in the art can, using the preceding description, utilize the present invention to its fullest extent. The following preferred specific embodiments are, therefore, to be construed as merley illustrative, and not limitative of the remainder of the disclosure in any way whatsoever. In the following examples, all temperatures are set forth uncorrected in degrees Celsius; unless otherwise indicated, all parts and percentages are by weight.

In another aspect, the diagnostic media and salts per se of this invention include any of those compounds wherein at least one Y is not a metal equivalent of said atomic numbers and is not H, i.e., is a cation of an inorganic or organic base or basic amino acid.

An especially preferred salt of this invention, inter alia, is that of example 5 (Production of the di-N-Methylglucamine salt of gadolinium(III) complex of diethylenetriamine-N,N,N',N'',N''-pentaacetic acid, $C_{28}H_{54}GdN_5O_{20}$).

EXAMPLE 1

Production of the gadolinium(III) complex of nitrilo-N,N,N-triacetic acid $C_6H_6GdNO_6$ The suspension of 36.2 g (=100 mmoles) of gadolinium oxide ($Gd_2O_3$) and 38.2 g (=200 mmoles) of nitrilotriacetic acid in 1.2 liters of water is heated to 90° C. to 100° C. with stirring and is stirred at this temperature for 48 hours. Then the insoluble part is filtered off with activated carbon and the filtrate is evaporated to dryness. The amorphous residue is pulverized.

Yield: 60 g; (87% of theory)

Melting point: 300° C.

Gadolinium: calculated, 45.5%; found, 44.9%

The iron(III) complex of nitrilo-N,N,N-triacetic acid is obtained with the aid of iron(III) chloride, $FeCl_3$.

EXAMPLE 2

Production of the disodium salt of gadolinium(III) complex of 13,23-dioxo-15,18,21-tris(carboxymethyl)-12,15,18,21,24-pentaazapentatriacontanedioic acid, $C_{36}H_{60}GdN_5O_{12}.2Na$ 15.2 g (=20 mmoles) of 13,23-dioxo-15,18,21-tris(carboxymethyl)-12,15,18,21,24-pentaazapentatriacontanedioic acid are suspended in 400 ml of water and heated to 95° C. 7.43 g (=20 mmoles) of gadolinium-(III) chloride hexahydrate, dissolved in 60 ml of water, are slowly added drop by drop. It is kept at this temperature for 2 hours and then mixed with 60 ml of 1N sodium hydroxide solution to neutralize the resulting hydrocloric acid.

After complete reaction (tresting with xylenol orange), the resulting precipitation is filtered and washed with water until free of chloride. 17.60 g (96% of theory) of a white powder, insoluble in water, with a melting point of 290°-292° C. are obtained.

Gadolinium(III) complex of 13,23-dioxo-15,18,21-tris(carboxymethyl)-12,15,18,21,24-pentaazapentatriacontanedioic acid.

Analysis: (Calculated) C 47.30; H 6.84; N 7.66; Gd 17.20; (Found) C 47.13; H 6.83; N 7.60; Gd 17.06.

14.6 g (=16 mmoles) of the gadolinium(III) complex thus obtained are suspended in 200 ml of water and mixed drop by drop with 31.4 ml of 1N sodium hydroxide solution. After 1 hour, a clear solution is obtained, filtered and then concentrated in vacuo. After drying in vacuo at 80° C., 13.2 g (87% of theory) of a white powder, with good aqueous solubility and a melting point of 279°-285° C., are obtained.

Analysis: (Calculated) C 45.13; H 6.31; N 7.31; Gd 16.41; Na 4.80; (Found) C 45.20; H 6.12; N 7.28; Gd 16.26; Na 4.75.

Similarly, di-N-methylglucamine salt of gadolinium-(III) complex of 13,23-dioxo-15,18,21-tris(carboxymethyl)-12,15,18,21,24-pentaazapentatriacontanedioic acid, $C_{50}H_{96}GdN_7O_{22}$ is obtained with N-methylglucamine instead of sodium hydroxide solution.

EXAMPLE 3

Production of the disodium salt of gadolinium(III) complex of 3,9-bis(1-carboxyethyl)-6-carboxymethyl-3,6,9-triazaundecanedioic acid, $C_{16}H_{22}GdN_3O_{10}.2Na$ 36.2 g (=0.1 mole) of gadolinium(III) oxide and 84.2 g (=0.2 mole) of 3,9-bis(1-carboxyethyl)-6-carboxymethyl-3,6,9-triazaundecanedioic acid are suspended in 250 ml of water and refluxed for 1 hour. The small amount of insoluble material is filtered off and the solution is concentrated to dryness in vacuo. The residue is pulverized and dried at 60° C. in vacuo. 112.8 g (=98% of theory) of the chelate are obtained as white powder.

Analysis: $C_{16}H_{24}GdN_3O_{10}$: (Calculated) C 33.39; H 4.20; Gd 27.32; N 7.30; (Found) C 33.25; H 4.49; Gd 27.42; N 7.21.

57.6 g (=0.1 mole) of the chelate are introduced in a solution of 0.1 mole of sodium hydroxide in 100 ml of water. The solution is set at a pH of 7.5 by addition of another 0.1 mole of sodium hydroxide powder, the solution is heated to boiling and ethyl alcohol is added drop by drop until permanent clouding. After several hours of stirring in an ice bath, the crystallizate is suctioned off, washed with ethyl alcohol and dried in vacuo. The disodium salt is obtained as a white powder in quantitative yield.

Analysis: (Calculated) C 31.02; H 3.58; Gd 25.38; N 6.78; (Found) C 31.10; H 3.71; GD 25.50; N 6.61.

EXAMPLE 4

Production of the dimorpholine salt of gadolinium(III) complex of 3,9-bis(1-carboxyethyl)-6-carboxymethyl-3,6,9-triazaundecanedioic acid, $C_{24}H_{42}GdN_5O_{12}$ 17.4 g (=0.2 mole) of morpholine are dissolved in 50 ml of water. 42.1 g (=0.1 mole) of 3,9-bis(1-carboxyethyl)-6-carboxymethyl-3,6,9-triazaundecanedioic acid and then 18.2 g (=0.05 mole) of gadolinium(III) oxide are added and refluxed until a clear solution occurs. Then acetone is added drop by drop by drop until a permanent clouding. After several hours stirring in an ice bath, the crystallizate is suctioned off, washed with acetone and dried in vacuo. Dimorpholine salt is obtained in quantitative amount as a white powder.

Analysis: (Calculated) C 38.44; H 5.65; Gd 20.97; N 9.34; (Found) C 38.31; H 5.72; Gd 20.76; N 9.32.

EXAMPLE 5

Production of the di-N-Methylglucamine salt of gadolinium(III) complex of diethylenetriamine-N,N,N',N'',N'''-pentaacetic acid, $C_{28}H_{54}GdN_5O_{20}$ 39.3 g (=100 mmoles) of diethylenetriamine-N,N,N',N'',N'''-pentaacetic acid are suspended in 200 ml of water and mixed with 19.5 g (=100 mmoles) of N-methylglucamine. Then 18.12 g (=50 mmoles) of gadolinium(III) oxide, $Gd_2O_3$ are added in portions and the resulting suspension is heated to 95° C. After about 1 hour, it is mixed with another 19.5 g (=100 mmoles) of N-methylglucamine and, after two more hours of heating, a clear solution is obtained. After complete reaction (testing with xylenol orange) it is filtered from the small amount of undissolved material and the filtrate is concentrated in vacuo to dryness. The residue is again dissolved in 100 ml of water and stirred into 250 ml of ethyl alcohol. After several hours of cooling, the crystallizate is suctioned off, washed with cold ethyl alcohol and dried at 60° in vacuo. 92.7 g (99% of theory) of a white powder with an uncharacteristic melting point is obtained.

Analysis: (Calculated) C 35.85; H 5.80; N 7.47; Gd 16.77; (Found) C 35.50; H 5.72; N 7.20; Gd 16.54.

Acetone, propyl alcohol or isopropyl alcohol can also be used instead of ethyl alcohol for purifying the complex salt.

Correspondingly, there are obtained:
with dysprosium(III) oxide, $Dy_2O_3$
di-N-methylglucamine salt of dysprosium(III) complex of diethylenetriamine-N,N,N',N'',N'''-pentaacetic acid, $C_{28}H_{54}DyN_5O_{20}$;
with lanthanum(III) oxide, $La_2O_3$
di-N-methylglucamine salt of lanthanum(III) complex of diethylenetriamine-N,N,',N'',N'''-pentaacetic acid, $C_{28}H_{54}LaN_5O_{20}$;
with ytterbium(III) oxide, $Yb_2O_3$
di-N-methylglucamine salt of ytterbium(III) complex of diethylenetriamine-N,N,N',N'',N'''-pentaacetic acid, $C_{28}H_{54}YbN_5O_{20}$
with samarium(III) oxide, $Sm_2O_3$ di-N-methylglucamine salt of samarium(III) complex of diethylenetriamine-N,N,N',N'',N'''-pentaacetic acid, $C_{28}H_{54}SmN_5O_{20}$;

with holmium(III) oxide, $Ho_2O_3$ di-N-methylglucamine salt of holmium(III) complex of diethylenetriamine-N,N,N',N'',N'''-pentaacetic acid, $C_{28}H_{54}HoN_5O_{20}$;

with bismuth(III) oxide, $Bi_2O_3$ di-N-methylglucamine salt of bismuth(III) complex of diethylenetriamine-N,N,N',N'',N'''-pentaacetic acid, $C_{28}H_{54}BiN_5O_{20}$;

with gadolinium(III) oxide, $Gd_2O_3$ tri-N-methylglucamine salt of gadolinium(III) complex of triethylenetetraamine-N,N,N',N'',N''',N'''-hexaacetic acid, $C_{39}H_{78}GdN_7O_{27}$;

Further, there are obtained:

with holmium(III) oxide, $Ho_2O_3$ and ethanolamine instead of N-methylglucamine diethanolamine salt of holmium(III) complex of diethylenetriamine-1N,N,N',N'',N'''-pentaacetic acid, $C_{18}H_{34}HoN_5O_{12}$;

with gadolinium(III) oxide, $Gd_2O_3$ and lysine instead of N-methylglucamine dilysine salt of gadolinium(III) complex of diethylenetriamine-N,N,N',N'',N'''-pentaacetic acid, $C_{26}H_{48}GdN_7O_{14}$.

With the use of diethanolamine the di-diethanolamine salt of holmium(III) complex of diethylenetriamine-pentaacetic acid, $C_{22}H_{42}HoN_5O_{14}$.

The salts appear as white powders with an uncharacteristic melting point.

EXAMPLE

Production of the disodium salt of gadolinium(III) complex of diethylenetriamine-N,N,N',N'',N'''-pentaacetic acid, $C_{14}H_{18}GdN_3O_{10}.2Na$ 18.2 g (=0.05 mole) of gadolinium(III) oxide and 39.3 g (=0.1 mole) of diethylenetriaminepentaacetic acid are suspended in 110 ml of water and refluxed for 1 hour. The clear solution is cooled and brought to pH 7.5 by addition of about 80 ml of 5N sodium hydroxide solution. It is again heated to boiling and 250 ml of ethyl alcohol are added drop by drop. After several hours of stirring in an ice bath, the crystallizate is suctioned off, washed with ice-cold ethyl alcohol and dried in vacuo at 60° C. A white powder, that does not melt up to 300° C., is obtained in quantitative amount.

Analysis: (Calculated) C 28.43; H 3.07; N 7.10; Gd 26.58; (Found) C 28.35; H 2.95; N 7.05; Gd 26.37.

In a corresponding way, there are obtained: with dyprosium(III) oxide, $Dy_2O_3$ disodium salt of dyprosium(III) complex of diethylenetriamine-N,N,N',N'',N'''-pentaacetic acid, $C_{14}H_{18}LaN_3O_{10}.2Na$;

with lanthanum(III) oxide, $La_2O_3$ disodium salt of lanthanum(III) complex of diethylenetriamine-N,N,N',N'',N'''-pentaacetic acid, $C_{14}H_{18}LaN_3O_{10}.2Na$;

with holmium(III) oxide, $Ho_2O_3$ disodium salt of holmium(III) complex of diethylenetriamine-N,N,N',N'',N'''-pentaacetic acid, $C_{14}H_{18}HoN_3O_{10}.2Na$;

with ytterbium(III) oxide, $Yb_2O_3$ disodium salt of ytterbium(III) complex of diethylenetriamine-N,N,N',N'',N'''-pentaacetic acid, $C_{14}H_{18}YbN_3O_{10}.2Na$;

with samarium(III) oxide, $Sm_2O_3$ disodium salt of samarium(III) complex of diethylenetriamine-N,N,N',N'',N'''-pentaacetic acid, $C_{14}H_{18}SmN_3O_{10}.2Na$;

with erbium(III) oxide, $Eb_2O_3$ disodium salt of erbium(III) complex of diethylenetriamine-N,N,N',N'',N'''-pentaacetic acid, $C_{14}H_{18}EbN_3O_{10}.2Na$;

with gadolinium(III) oxide, $Gd_2O_3$ sodium salt of digladolinium(III) complex of tetraethylenepentamine-N,N,N',N'',N''',N'$^v$,N'$^v$-heptaacetic acid, $C_{22}H_{30}Gd_2N_5O_{14}.Na$.

These salts appear as white powders with an uncharacteristic melting point and have a very good aqueous solubility.

EXAMPLE 7

Production of the N-methylglucamine salt of iron(III) complex of diethylenetriaminepentaacetic acid, $C_{21}H_{37}FeN_4O_{15}$ 35.40 g (=90 mmoles) of diethylenetriaminepentacetic acid are suspended in 100 ml of water and mixed with 24.3 g (=90 mmols) of iron(III) chloride hexahydrate ($FeCl_3.6H_2O$) dissolved in 100 ml of water. The suspension, which is dark brown at first, is heated to 95° C. After about 1 hou, the color changes to light yellow. 270 ml of 1N sodium hydroxide solution is added to neutralize the resulting hydrochloric acid and it is heated for another 3 hours to 95° C. The resulting light yellow precipitate is suctioned off, washed with water until free of chloride and dried in vacuo at 60° C. 17.85 g (45% of theory) of a light yellow powder, with a melting point of >300° C., is obtained.

17.85 g (=40 mmoles) of the resulting iron(III) complex are suspended in 200 ml of water and thoroughly mixed in portions with 7.8 g (=40 mmoles) of N-methylglucamine. It is heated for about 3 hours to 50° C. and a nearly clear, reddish brown solution is obtained, which is filtered and then concentrated in vacuo to dryness. The residue is dried in vacuo at 50° C. 24.3 g (95% of theory) of a reddish brown powder with a melting point of 131°–133° C. are obtained.

Analysis: (Calculated) C 39.82; H 5.89; N 8.85; Fe 8.81; (Found) C 39.70; H 6.00; N 8.65; Fe 9.01.

With sodium hydroxide solution instead of the organic bases, there are obtained:

sodium salt of iron(III) complex of ethylenediaminetetraacetic acid, $C_{10}H_{12}FeN_2O_8.Na$ sodium salt of iron(III) complex of trans-1,2-cyclohexenediaminetetraacetic acid, $C_{14}H_{18}FeN_2O_8.Na$ disodium of iron(III) complex of diethylenetrinitrilopenta(methanephosphonic acid), $C_9H_{23}FeN_3O_{15}P_5.2Na$ sodium salt of iron(III) complex of 1,10-diaza-4,7-dioxadecane-1,1,10,10-tetraacetic acid, $C_{14}H_{20}FeN_2O_{10}.Na$ sodium salt of iron(III) complex of ethylenediaminetetraacethydroxamic acid, $C_{10}H_{16}FeN_6O_8.Na$ In a corresponding way, there are obtained with N-methylglucamine:

di-N-methylglucamine salt of iron(III) complex of diethylenetriamine-N,N,N',N'',N''-pentaacetic acid, $C_{28}H_{54}FeN_5O_{20}$ N-methylglucamine salt of iron(III) complex of trans-1,2-cyclohexenediamine-N,N,N',N'-tetraacetic acid, $C_{21}H_{36}FeN_3O_{13}$ N-methyleglucamine salt of iron(III) complex of ethylenediamine-N,N,N',N'-tetraacetic acid, $C_{17}H_{30}FeN_3O_{13}$ tri-N-methylglucamine salt of iron(III) complex of triethylenetriamine-N,N,N',N'',N'''-hexaacetic acid, $C_{39}H_{78}FeN_7O_{27}$.

With the use of diethanolamine instead of N-methylglucamine, didiethanolamine salt of iron(III) complex of diethylenetriamine-N,N,N'',N'',N'''-pentaacetic acid, $C_{22}H_{42}FeN_5O_{14}$ is obtained.

EXAMPLE 8

Production of the N-methylglucamine salt of gadolinium(III) complex of trans-1,2-cyclohexenediamine-N,N,N',N'-tetraacetic acid, $C_{21}H_{36}GdN_3O_{13}$ 20.78 g (=60 mmoles) of trans-1,2-cyclohexenediamine-N,N,N',N'-tetraacetic acid are suspended in 150 ml of water. After addition of 11.7 g (=60 mmoles) of N-methylglucamine, a nearly clear solution is obtained, to which 10.88 g (=30 mmoles) of gadolinium oxide ($Gd_2O_3$) are added. The newly resulting suspension is heated for 6 hours to 95° C. It is filtered off from the small amount of undissolved material and the filtrate concentrated to dryness. The residue is dried in vacuo at 60° C. and pulverized. 38.6 g (92% of theory) of a white powder with a melting point of 258°–261° C. are obtained.

Analysis: (Calculated) C 36.25; H 5.22; N 6.04; Gd 22.60; (Found) C 36.40; H5.50; N 5.98; Gd 22.52.

In a similar way, the sodium salt of gadolinium(III) complex of trans-1,2-cyclohexenediamine-N,N,N', N'-tetraacetic acid, $C_{14}H_{18}GdN_2O_8 \cdot Na$ is obtained with sodium hydroxide solution instead of N-methylglucamine.

The sodium salt of chromium(III) complex of ethylenediamine-N,N,N',N'-tetraacetic acid, $C_{10}H_{12}CrN_2O_8 \cdot Na$ is obtained with freshly precipitated chromium(III) hydroxide, $Cr(OH)_3$.

EXAMPLE 9

Production of the dosodium salt of manganese(II) complex of trans-1,2-cyclohexylenediamine-N,N,N',N'-tetraacetic acid, $C_{14}H_{18}MnN_2O_8 \cdot 2Na$ 34.6 g (=100 mmoles) of trans-1,2-cyclohexenediamine-N,N,N',N'-tetraacetic acid are suspended under nitrogen in 100 ml of water and mixed with 11.5 g (=100 mmoles) of manganese(II) carbonate, $MnCO_3$. It is heated to 95° C. and 200 ml of 1N sodium hydroxide solution are added drop by drop. The clear solution is concentrated in vacuo and the residue dried in vacuo at 60° C. 40.8 g (92% of theory) of a pink powder are obtained.

Analysis: (Calculated) C 37.94; H 4.09; N 6.32; Mn 12.40; (Found) C 37.78; H 4.12; N 6.20; Mn 12.31.

In a corresponding way there are obtained:
from copper(II) carbonate the disodium salt of copper(II) complex of trans-1,2-cyclohexenediaminetetraacetic acid, $C_{14}H_{18}CuN_2O_8 \cdot 2Na$;

from cobalt(II) carbonate the disodium salt of cobalt-(II) complex of trans-1,2-cyclohexenediaminetetraacetic acid, $C_{14}H_{18}CoN_2O_8 \cdot 2Na$;

from nickel(II) carbonate the disodium salt of nickel-(II) complex of trans-1,2-cyclohexenediaminetetraacetic acid, $C_{14}H_{18}NiN_2O_8 \cdot 2Na$.

With N-methylglucamine instead of sodium hydroxide solution, the following are obtained:
di-N-methylglucamine salt of manganese(II) complex of trans-1,2-cyclohexenediaminetetraacetic acid, $C_{28}H_{54}MnN_4O_{18}$;

di-N-methylglucamine salt of manganese(II) complex of dl-2,3-butylenediaminetetraacetic acid, $C_{26}H_{52}MnN_4O_{18}$;

di-N-methylglucamine salt of manganese(II) complex of ethylenediamine-N,N,N',N'-tetraacetic acid, $C_{24}H_{48}MnN_4O_{18}$;

di-N-methylglucamine salt of manganese(II) complex of dl-1,2-butylenediamine-N,N,N',N'-tetraacetic acid, $C_{26}H_{52}MnN_4O_{18}$;

di-N-methylglucamine salt of manganese(II) complex of dl-1,2-diaminopropane-N,N,N',N'-tetraacetic acid, $C_{25}H_{50}MnN_4O_{18}$;

tri-N-methylglucamine salt of manganese(II) complex of diethylenetriaminepentaacetic acid, $C_{35}H_{72}MnN_6O_{25}$;

with nickel(II) carbonate, $NiCO_3$
di-N-methlglucamine salt of nickel(II) complex of ethylenediamine-N,N,N',N'-tetraacetic acid, $C_{24}H_{48}NiN_4O_{18}$;

with cobalt(II) carbonate, $CoCO_3$ and ethanolamine diethanolamine salt of cobalt(II) complex of ethylenediamine-N,N,N',N'-tetraacetic acid, $C_{14}H_{28}CoN_4O_{10}$;

with copper(II) carbonate, $CuCO_3$, and ethanolamine diethanolamine salt of copper(II) complex of ethylenediamine-N,N,N',N'-tetraacetic acid, $C_{14}H_{28}CuN_4O_{10}$;

with manganese(II) carbonate, $MnCO_3$, and diethanolamine
tridiethanolamine salt of manganese(II) complex of diethylenetriamine-N,N,N',N'',N''-pentaacetic acid, $C_{26}H_{54}MnN_6O_{16}$;

with manganese(II) carbonate, $MnCO_3$, and morpholine
dimorpholine salt of manganese(II) complex of ethylenediamine-N,N,N'',N'''-tetraacetic acid, $C_{18}H_{32}MnN_4O_{10}$.

EXAMPLE 10

N-methylglucamine salt of gadolinium(III) complex of ethylenediamine-N,N,N',N'-tetraacetic acid, $C_{17}H_{30}GdN_3O_{13}$ 29.2 g (=100 moles) of ethylenediamine-N,N,N',N'-tetraacetic acid are suspended in 100 ml of water and heated to 95° C. with 18.1 g (=50 mmoles) of gadolinium(III) oxide. During heating up, 19.5 g (=100 mmoles) of N-methylglucamine are added by portions. After about 3 hours, a clear solution is obtained, which is filtered and concentrated in vacuo to dryness. The residue is dried in vacuo at 60° C. 61.3 g (95% of theory) of a white powder with an uncharacteristic melting point are obtained.

Analysis: (Calculated) C 31.82; H 4.71; N 6.55; Gd 24.51; (Found) C 31.65; H 4.59; N 6.52; Gd 24.56.

In an analogous way, there are obtained:
with dysprosium(III) oxide, $Dy_2O_3$

N-methylglucamine salt of dysprosium(III) complex of ethylenediamine-N,N,N',N'-tetraacetic, $C_{17}H_{30}DyN_3O_{13}$;

N-methylglucamine salt of gadolinium(III) complex of 1,10-diaza-4,7-dioxadecane-1,1,10,10-tetraacetic acid, $C_{21}H_{38}GdN_3O_{15}$;

N-methylglucamine salt of gadolinium(III) complex of 1,2-diphenylethylenediaminetetraacetic acid, $G_{29}H_{38}N_3O_{13}Gd$;

with lead(II) oxide, PbO, and sodium hydrochloride disodium salt of lead(II) complex of ethylenediaminetetraacetic acid, $C_{10}H_{12}N_2O_8Pb.2Na$;

with freshly precipitated chromium(III) hydroxide, $Cr(OH)_3.Na$ sodium salt of chromium(III) complex of ethylenediaminetetraacetic acid, $C_{10}H_{12}CrN_2O_8$; and analogously sodium salt of gadolinium(III) complex of ethylenediaminetetraacethydroxamic acid, $C_{10}H_{16}GdN_6O_8.Na$;

sodium salt of gadolinium(III) complex of ethylenediamine-N,N,N',N'-tetraacetic acid, $C_{10}H_{12}GdN_2O_8.Na$.

EXAMPLE 11

Production of the sodium salt of gadolinium(III) complex of 1,4,7,10-tetraazacyclododecane-N,N',N'',N'''-tetraacetic acid, $C_{16}H_{24}GdN_4O_8.Na$ 4.0 g (=10 mmoles) of 1,4,7,10-tetraazacyclododecane-N,N',N'',N'''-tetraacetic acid are suspended in 20 ml of water and mixed with 10 ml of 1N sodium hydroxide solution. 1.8 g (=5 mmoles) of gadolinium(III) oxide, $Gd_2O_3$, are added and the suspension is heated for 2 hours to 50° C. The clear solution is filtered and concentrated in vacuo. The residue is dried and pulverized. 5.5 g (95% of theory) of a white powder are obtained.

Analysis: (Calculated) C 33.10; H 4.17; N 9.65; Gd 27.08; (Found) C 33.01; H 4.20; N 9.57; Gd 27.16.

In a similar way, there are obtained:

N-methylglucamine salt of gadolinium(III) complex of 1,4,7,10-tetraazacyclododecane-N,N',N'',N'''-tetraacetic acid, $C_{23}H_{42}GdN_5O_{13}$ sodium salt of gadolinium(III) complex of 1,4,8,11-tetraazacyclotetradecane-N,N',N',N'''-tetraacetic acid, $C_{18}H_{28}GdN_4O_8.Na$.

EXAMPLE 12

Production of the tetra-N-methylglucamine salt of gadolinium(III) complex of ethylenedinitrilo-tetrakis(methanephosphonic acid), $C_{34}H_{85}GdN_6O_{32}P_4$ 9.11 g (=20 mmoles) of ethylenedinitrilo-tetrakis(methanephosphonic acid) are suspended in 150 ml of water and adjusted to a pH of 5 with a suitable amount of N-methylglucamine. 3.6 g (=10 mmoles) of gadolinium(III) oxide, $Gd_2O_3$, are added and heated to 70° C. After about 1 hour a clear solution is obtained, which is mixed with the remaining portion of N-methylglucamine. Altogether, 15.6 g (=80 mmoles) of N-methylglucamine are used. The solution is concentrated in vacuo to dryness and the remaining gelatinous residue is added to 200 ml of acetonitrile. It is stirred at 30° C. for about 20 hours and the resulting fine precipitate is suctioned off. After drying in vacuo at 40° C., 23.4 g (85% of theory) of a white power with a melting point of 115°–118° C. are obtained.

Analysis: (Calculated) C 29.78; H 6.25; N 6.13; P 9.04; Gd 11.47; (Found) C 29.85; H 6.57; N 5.98; P 8.78; Gd 11.26.

In a similar way, there are obtained:

hepta-N-methylglucamine salt of gadolinium(III) complex of diethylenetriamine-N,N,N',N'',N''-penta(methanephosphonic acid), $C_{58}H_{144}GdN_{10}O_{50}P_5$ and with the use of sodium hydroxide solution instead of N-methylglucamine disodium salt of gadolinium(III) complex of diethylenetrinitrilopenta(methanephosphonic acid), $C_9H_{23}GdN_3O_{15}P_5.2Na$

EXAMPLE 13

Production of the disodium salt of manganese(II) complex of ethylenedinitrilotetra(acethydroxamic acid), $C_{10}H_{16}MnN_6O_8.2Na$ 2.30 g of manganese(II) carbonate and 7.05 g of ethylenedinitrilotetra(acethydroxamic acid) are refluxed in 18 ml of water for 3 hours. Then the pH is adjusted to 7 by addition of dilute sodium hydroxide solution and 40 ml of acetone are added drop by drop. After several hours of stirring in an ice bath, the precipitated crystallizate is suctioned off, washed with acetone and dried at 50° C. in vacuo. A dihydrate is obtained in quantitative amount as a white powder with a melting point above 300° C.

Mn: (Calculated) 11.30; (Found) 11.12.

EXAMPLE 14

Production of a mixed salt solution of sodium and N-methylglucamine salt of gadolinium(III) complex of diethylenetriaminepentaacetic acid (a) Production of the mono-N-methylglucamine salt of the complex, $C_{21}H_{37}GdN_4O_{15}$ 195.2 g (1 mole) of N-methylglucamine are dissolved in 7 liters of water. Then 393.3 g (1 mole) of diethylenetriaminepentaacetic acid and 181.3 g (0.5 mole) of gadolinium oxide, $Gd_2O_3$, are added and refluxed for 2 hours. The filtered clear solution is spray dried. A white crystalline powder with a water content of 2.6%, which sinters at 133° C. and melts with foaming at 190° C. is obtained.

Gd: (Calculated) 21.17; (Found) 21.34.

(b) Production of the neutral mixed salt solution 730.8 g (=1 mole) of the salt obtained under (a) are suspended in 630 ml of water p.i. (pro injectione, i.e., sterile) and 40 g (=1 mole) of sodium hydroxide powder are added in portions. Water p.i. is added to the neutral solution to make 1000 ml, it is put into bottles through a pyrogen filter and sterilized by heat. This one molar solution contains 753.8 g of mixed salt per liter.

EXAMPLE 15

Production of a solution of the di-N-methylglucamine salt of gadolinium(III) complex of diethylenetriaminepentaacetic acid 535.0 g (=730 mmoles) of the salt described in example 5 are made into a paste in 500 ml of water p.i. and brought to solution by addition of 142.4 g (=730 mmoles) of N-methylglucamine at pH 7.2. Then water p.i. is added to make 1000 ml, the solution is put into ampoules and sterilized by heating.

EXAMPLE 16

Production of a solution of the disodium salt of gadolinium(III) complex of diethylenetriaminepentaacetic acid 485.1 g (=820 mmoles) of the disodium salt obtained in example 6 are made into a paste in 500 ml of water p.i. Then water p.i. is added to make 1000 ml, the solution is put into ampoules and sterilized by heating.

EXAMPLE 17

Production of a solution of the disodium salt of gadolinium(III) complex of 13,23-dioxo-15,18,21-tris(-carboxymethyl)-12,15,18,21,24-pentazapentatriacontanedioic acid 392.0 g (=400 mmoles) of the salt described in example 2 are made into a paste in 500 ml of water p.i. and dissolved by adding water p.i. to make 1000 ml with gentle heating. The solution is put into bottles and sterilized by heating.

EXAMPLE 18

Production of a solution of the N-methylglucamine salt of gadolinium(III) complex of 1,4,7,10-tetraazacyclododecanetetraacetic acid 370.9 g (=500 mmoles) of the salt mentioned in example 11 is made into a paste in 500 ml of water p.i. and dissolved by adding water p.i. to make 1000 ml. The solution is put into ampoules and sterilized by heating.

EXAMPLE 19

Production of a solution of the di-N-methylglucamine salt of manganese(II) complex of trans-1,2-cyclohexenediaminetetraacetic acid.

395.9 g (=500 mmoles) of the salt mentioned in example 9 are suspended in 500 ml of water p.i. It is mixed with 1.3 g of ascorbic acid and brought to solution by adding water p.i. to make 1000 ml. The solution is sterilized by filtration and put into ampoules.

EXAMPLE 20

Production of a solution of the tri-N-methylglucamine salt of manganese(II) complex of diethylenetriaminepentaacetic acid 514.4 g (=500 mmoles) of the salt mentioned in example 9 are suspended in 600 ml of water p.i. It is mixed with 1.3 g of ascorbic acid and dissolved by adding water p.i. to make 1000 ml. The solution is sterilized by filtering and put into ampoules.

EXAMPLE 21

Production of a solution of the di-N-methylglucamine salt of iron(III) complex of diethylenetriaminepentaacetic acid 44.6 g (=0.1 mole) of the iron(III) complex of diethylenetriaminepentaacetic acid obtained in example 7 are suspended in 40 ml of water p.i. After addition of 0.18 g of tromethamine hydrochloride and 39.1 g (=0.2 moles) of N-methylglucamaine it is dissolved to neutrality, water p.i. is added to the solution to bring it to 100 ml, it is put into ampoules and sterilized by heating.

EXAMPLE 22

Production of a solution of the gadolinium(III) complex of nitrilotriacetic acid 1.9 g (=10 mmoles) of nitrilotriacetic acid and 1.8 g (=5 mmoles) of gadolinium(III) oxide are dissolved in 100 ml of water p.i. with heating. The solution is put into ampoules and sterilized by heating.

EXAMPLE 23

Production of a solution of the N-methylglucamine salt of gadolinium(III) complex of ethylenediaminetetraacetic acid.

38.52 g (=60 mmoles) of the substance described in example 10 are dissolved in 70 ml of water p.i. After addition of 0.12 g of water p.i. is added to make 100 ml, the solution is put into ampoules and sterilized by heating.

EXAMPLE 24

Production of a solution of the di-N-methylglucamine salt of dysprosium(III) complex of diethylenetriaminepentaacetic acid 35.7 g (=60 mmoles) of the dysprosium(III) complex of diethylenetriaminepentaacetic acid (8.0% water content) are suspended in 70 ml of water p.i. and brought to solution by addition of 21.2 g (=120 mmoles) of N-methylglucamaine at a pH of 7.5. Then water p.i. is added to make 100 ml, the solution is put into ampoules and sterilized by heating.

EXAMPLE 25

Production of a solution of the N-methylglucamine salt of gadolinium(III) complex of trans-1,2-cyclohexenediaminetetraacetic acid 555.8 g (=0.8 mole) of the salt described in example 8 are dissolved in water p.i. to make 1000 ml. After filtration through a pyrogen filter, the solution is put into ampoules and sterilized by heating.

EXAMPLE 26

Production of a solution of the N-methylglucamine salt of ruthenium(III) complex of 1,10-diaza-4,7-dithiadecane-1,1,10,10-tetraacetic acid 15.6 g (=0.03 mole) of the ruthenium(III) complex of 1,10-diaza-4,7-dithiadecane-1,1,10,10-tetraacetic acid are suspended in 50 ml of water p.i. and brought to solution at pH 7.5 by addition of 5.9 g (=0.03 moles) of N-methylglucamine. Water p.i. is added to make 1000 ml, the solution is put into ampoules and sterilized by heating.

EXAMPLE 27

Production of a solution of the dilysine salt of gadolinium(III) complex of diethylenetriaminepentaacetic acid 273.8 g (=0.5 mole) of the gadolinium(III) complex of diethylenetriaminepentaacetic acid are suspended in 500 ml of water p.i. 292.4 g (=1 mole) of lysine are added, left to stir for several hours with gentle heating and then water p.i. is added to make 1000 ml. The solution is put in bottles and sterilized by heating.

EXAMPLE 28

Production of a solution of the tri-N-methyglucamine salt of molybdenum (VI) complex of diethyelenetriaminepentaacetic acid 18.8 g (=0.28 mole) of the complex $H_3[Mo_2O_2(OH)_4.C_{14}H_{23}N_3O_{120}]$ are suspended in 50 ml of water p.i. and dissolved to neutrality by addition of 16.4 g (=0.84 mole) of N-methylglucamine. 0.15 g of tromethamine is added, water p.i. is added to make 100 ml, the solution is subjected to sterilization by filtering and put into ampoules.

EXAMPLE 29

Production of a solution of the disodium salt of manganese(II) complex of ethylenediaminetetraacetic acid 343.2 g (=1 mole) of the manganese(II) complex of ethylenediaminetetraacetic acid are suspended in 500 ml of water p.i. and dissolved to neutrality by addition by portions of 80 g (=2 moles) of sodium hydroxide. After addition of 1.5 g of tromethamine, water p.i. is added to the solution to make 1000 ml, it is put into bottles and sterilized by heating.

EXAMPLE 30

Production of a solution of the sodium salt of iron(III) complex of ethylenediaminetetraacetic acid 345.7 g (=1 mole) of the iron(III) complex of ethylenediaminetetraacetic acid are suspended in 500 ml of water p.i. and dissolved to neutrality by addition by portions of 40 g (=1 mole) of sodium hydroxide. After addition of 1.5 g of tromethamine, water p.i. is added to the solution to make 1000 ml, it is put in bottles and sterilized by heating.

EXAMPLE 31

Production of a solution of the disodium salt of iron(III) complex of diethylenetriaminepentaacetic acid 334.6 g (=0.75 mole) of the iron(III) complex of diethylenetriaminepentaacetic acid are suspended in 500 ml of water p.i. and dissolved to neutrality by addition by portions of 60 g (=1.5 moles) of sodium hydroxide. Water p.i. is added to the solution to make 1000 ml, it is put into bottles and sterilized by heating.

EXAMPLE 32

Production of a solution of the sodium salt of gadolinium(III) complex of trans-1,2-cyclohexenediaminetetraacetic acid 558.6 (=1 mole) of the salt mentioned in example 8 are dissolved in water p.i. to 1000 ml. The solution is put into bottles and sterilized by heating.

EXAMPLE 33

Production of a solution of the N-methylglucamaine salt of gadolinium(III) complex of 1,2-diphenylethylenediaminetetraacetic acid 396.9 g (=500 mmoles) of the salt described in example 10 are made into a paste in 600 ml of water p.i. and dissolved by addition of water to make 1000 ml. The solution is put into ampoules and sterilized by heating.

EXAMPLE 34

Production of a solution of the sodium salt of iron(III) complex of ethylenediaminetetraacetic acid 183.5 g (=500 mmoles) of the salt mentioned in example 7 are made into a paste in 500 ml of water p.i. 1.0 g of tromethamine is added, water p.i. is added to make 1000 ml, the solution is put into ampoules and sterilized by heating.

EXAMPLE 35

Production of a solution of the di-N-methylglucamine salt of lanthanum(III) complex of diethylenetriaminepentaacetic acid 459.8 g (=500 mmoles) of the salt mentioned in example 5 are made into a paste in 650 ml of water p.i. and brought to solution by addition of water p.i. to make 1000 ml. The solution is put into ampoules and sterilized by heating.

EXAMPLE 36

Production of a solution of the di-N-methylglucamine salt of bismuth(III) complex of diethylenetriaminepentaacetic acid 692.8 g (=700 mmoles) of the salt mentioned in example 5 are made into a paste in 600 ml of water p.i. and after addition of 1.8 g of tromethamine dissolved by addition of water p.i. to make 1000 ml with gentle heating. The solution is put into ampoules and sterilized by heating.

EXAMPLE 37

Production of a solution of the di-N-methylglucamine salt of holmium(III) complex of diethylenetriaminepentaacetic acid 662.0 g (=700 mmoles) of the salt mentioned in example 5 are made into a paste in 600 ml of water p.i. and after addition of 1.8 g of tromethamine, are dissolved by addition of water p.i. to make 1000 ml with gentle heating. The solution is put into ampoules and sterilized by heating.

EXAMPLE 38

Production of a solution of the di-N-methylglucamine salt of ytterbium(III) complex of diethylenetriaminepentaacetic acid 476.9 g (=500 mmoles) of the salt mentioned in example 5 are made into a paste in 650 ml of water p.i. and after addition of 1.5 g of tromethamine dissolved by addition of water p.i. to make 1000 ml. The solution is put into ampoules and sterilized by heating.

EXAMPLE 39

Production of a solution of the disodium salt of lanthanum(III) complex of diethylenetriaminepentaacetic acid 573.2 g (=1000 mmoles) of the salt mentioned in example 6 are made into a paste in 650 ml of water p.i. and dissolved by addition of water p.i. to make 1000 ml. The solution is put into ampoules and sterilized by heating.

EXAMPLE 40

Production of a solution of the disodium salt of dysprosium(III) complex of diethylenetriaminepentaacetic acid.

477.4 g (=800 mmoles) of the salt mentioned in example 6 are made into a paste in 600 ml of water p.i. and dissolved by addition of water p.i. to make 1000 ml. The solution is put into ampoules and sterilized by heating.

EXAMPLE 41

Production of a solution of the disodium salt of holmium(III) complex of diethylenetriaminepentaacetic acid 299.6 g (=500 mmoles) of the salt mentioned in example 6 are made into a paste in 500 ml of water p.i. and dissolved by addition of water p.i. to make 1000 ml. The solution is put into ampoules and sterilized by heating.

EXAMPLE 42

Production of a solution of the disodium salt of ytterbium(III) complex of diethylenetriaminepentaacetic acid.

303.5 g (=500 mmoles) of the salt mentioned in example 6 are made into a paste in 500 ml of water p.i. and dissolved by addition of water p.i. to make 1000 ml. The solution is put into ampoules and sterilized by heating.

EXAMPLE 43

Production of a solution of the tetra-N-methylglucamine salt of gadolinium(III) complex of ethylenedinitrilo-tetrakis(methanephosphonic acid)

137.1 g (=100 mmoles) of the salt mentioned in example 12 are made into a paste in 500 ml of water p.i. and after addition of 0.8 g of tromethamine are dissolved by addition of water p.i. to make 1000 ml. The solution is put into ampoules and sterilized by heating.

EXAMPLE 44

Production of a solution of gadolinium(III) complex of N'-(2-hydroxyethyl)ethylenediamine-N,N,N'-triacetic acid 1.9 g (=6.7 mmoles) of N'-(2-hydroxyethyl)ethylenediamine-N,N,N'-triacetic acid and 1.2 g (=3.35 moles) of gadolinium(III) oxide are dissolved in 6 ml of water p.i. with heating. The solution is put into ampoules and sterilized by heating.

EXAMPLE 45

Production of a solution of the disodium salt of manganese(II) complex of trans-1,2-cyclohexenediaminetetraacetic acid 44.3 g (=100 mmoles) of the salt mentioned in example 9 are made into a paste under nitrogen cover in 60 ml of water p.i. and brought to solution by addition of water p.i. to make 100 ml. The solution is put into ampoules and sterilized by heating.

EXAMPLE 46

Production of a solution of the sodium salt of gadolinium(III) complex of 1,4,8,11-tetraazacyclotetradecane-N',N',N'',N'''-tetraacetic acid 552.6 g (=1 mole) of the salt mentioned in example 11 are dissolved in water p.i. to make 1000 ml. The solution is put into bottles and sterilized by heating.

EXAMPLE 47

Production of a solution of the disodium salt of bismuth(III) complex of diethylenetriaminepentaacetic acid.

23.4 g (=50 mmoles) of bismuth(III) oxide are suspended in 50 ml of water p.i. After addition of 39.3 g (=100 mmoles) of diethylenetriaminepentaacetic acid and 4.0 g (=50 mmoles) of sodium hydroxide, it is refluxed to a clear solution. The solution, cooled to room temperature, is neutralized by addition of 4.0 g of sodium hydroxide and water p.i. is added to make 100 ml. The solution is put into ampoules and sterilized by heating.

EXAMPLE 48

Production of a solution of the disodium salt of samarium(III) complex of diethylenetriaminepentaacetic acid 58.5 g (=100 mmoles) of the salt mentioned in example 6 are dissolved in 65 ml of water p.i. with heating. Water p.i. is added to make a total volume of 100 ml, it is put into ampoules and sterilized by heating.

EXAMPLE 49

Production of a solution of the di-N-methylglucamine salt of gadolinium(III) complex of 13,23-dioxo-15,18,21-tris(carboxymethyl)-12,15,18,21,24-pentaazatriacontanedioic acid 130.4 g (=100 mmoles) of the salt mentioned in example 2 are made into a paste in 250 ml of water p.i. and dissolved with heating. Water p.i. is added to make 500 ml, the solution is put into ampoules and sterilized by heating.

EXAMPLE 50

Production of a solution of the di-N-methylglucamine salt of manganese(II) complex of ethylenediaminetetraacetic acid 3.68 g (=5 mmoles) of the substance described in example 9 are dissolved in 70 ml of water p.i. and the solution is mixed with 0.4 g of sodium chloride. Then water p.i. is added to make 100 ml and the solution is put into ampoules through a sterilizing filter. The solution is isotonic with the blood with 280 mOsm.

EXAMPLE 51

Production of a solution of the disodium salt of gadolinium(III) complex of diethylenetrinitrilopenta(methanephosphonic acid)

38.57 g (=50 mmoles) of the substance described in example 12 are made into a paste in 50 ml of water p.i. The pH is adjusted to 7.2 by addition of sodium hydroxide powder, and water p.i. is added to make 100 ml. The solution is put into ampoules and sterilized by heating.

EXAMPLE 52

Production of a solution of the trisodium salt of manganese(II) complex of diethylenetriaminepentaacetic acid.

39.3 g (=100 mmoles) of diethylenetriaminepentaacetic acid are suspended in 100 ml of water p.i. under nitrogen and mixed with 11.5 g of manganese(II) carbonate. It is heated to 95° C. and 300 ml of 1N sodium hydroxide solution are added drop by drop. The neutral solution is sterilized by filtering and put into ampoules.

EXAMPLE 53

Composition of a powder for protection of a suspension

---

4.000 g    gadolinium(III) complex of diethylenetriaminepentaacetic acid (water content 8.0%)

|       |                                      |
|-------|--------------------------------------|
| 3.895 g | saccharose                         |
| 0.100 g | polyoxyethylenepolyoxypropylene polymer |
| 0.005 g | aromatics                          |
| 8.000 g |                                    |

EXAMPLE 54

Production of a solution of a gadolinium(III) complex of the conjugate of diethylenetriaminepentaacetic acid with human serum albumin 10 mg of 1,5-bis(2,6-dioxomorpholino)-3-azapentane-3-acetic acid are added to 20 ml of a solution of 3 mg of protein in 0.05 molar sodium bicarbonate buffer (pH 7–8). It is allowed to stir for 30 minutes at room temperature and then dialyzed against a 0.3 molar sodium phosphate buffer. Then 50 mg of gadolium(III) acetate are added and purified by gel chromotography in a Sephadex G25 column. The resulting fraction is sterilized by filtering and put into Multivials. A storable dry product is obtained by freeze-drying.

The solution of the corresponding complex conjugate is obtained in a similar way with immunoglobulin.

EXAMPLE 55

Production of a solution of the gadolium(III) complex of the conjugate of diethylenetriaminepentaacetic acid (DTPA) with monoclonal antibodies 1 mg of a mixed DTPA-anhydride (obtained, for example, from DTPA and isobutyl chloroformate) is added to 20 pl of a solution of 0.3 mg of monoclonal antibodies in 0.05 molar sodium bicarbonate buffer (pH 7–8) and stirred for 30 minutes at room temperature. It is dialyzed against 0.3 molar sodium phosphate buffer and the resulting antibody fraction is mixed with 2 mg of the gadolinium(III) complex of ethylenediaminetetraacetic acid (EDTA). After purification by gel chromatography with Sephadex G25, the solution sterilized by filtering is put in Multivials and freeze-dried.

A solution of the corresponding gadolinium(III) complex of CDTA-antibodies is obtained in a similar way by using the mixed anhydride of trans-1,2-diaminocyclohexanetetraacetic acid (CDTA).

The manganese(II) complex of the antibodies coupled with DTPA or CDTA is obtained in a similar way by using the manganese(II) complex of ethylenediaminetetraacetic acid.

EXAMPLE 56

Production of a solution of the gadolinium(III) complex of the conjugate of 1-phenylethylenediaminetetraacetic acid with immunoglobulin By following the method described in J. Med. Chem. 1974, Vol. 17, p 1307, a 2% solution of protein in a 0.12 molar sodium bicarbonate solution, which contains 0.01 mole of ethylenediaminetetraacetic acid is cooled to +4° C. and mixed drop by drop with the protein equivalent portion of a freshly produced ice-cold diazonium salt solution of 1-(p-aminophenyl)ethylenediaminetetraacetic acid. It is allowed to stir overnight at +4° C. (pH 8.1) and then dialyzed against a 0.1 molar sodium citrate solution. After completion of the dialysis, the solution of the conjugate is mixed with an excess of gadolinium(III) chloride and ultrafiltered to remove ions. Then the solution sterilized by filtering is put into Multivials and freeze-dried.

EXAMPLE 57

Production of a colloidal dispersion of an Mn-CDTA-lipid conjugate 0.1 mmole of distearoylphosphatidylethanolamine and 0.1 mmole of bisanhydride of trans-1,2-diaminocyclohexanetetraacetic acid are stirred in 50 ml of water for 24 hours at room temperature. 0.1 mmole of manganese(II) carbonate is added and restirred for 6 hours at room temperature. After purification with a Sephadex G50 column, the solution sterilized by filtering is put into Multivials and freeze-dried.

A colloidal dispersion of the gadolinium-DTPA-lipid conjugate can be obtained in a similar way with gadolinium(III) oxide.

EXAMPLE 58

Production of liposomes loaded with gadolinium-DTPA

By following the method described in Proc. Natl. Acad. Sci. U.S.A. 75, 4194, a lipid mixture is produced from 75 mole % of egg phosphatidylcholine and 25 mole % of cholesterol as a dry substance. 500 mg of it are dissolved in 30 ml of diethylether and mixed drop by drop in an ultrasonic bath with 3 ml of a 0.1 molar solution of the di-N-methyglucamine salt of gadolinium(III) complex of diethylenetriaminepentaacetic acid in water p.i. After completre addition of the solution, the treatment with ultrasonic waves is continued for 10 more minutes and then concentrated in the Rotavapor. The gelatinous residue is suspended in 0.125 molar sodium chloride solution is freed of the unencapsulated contrast medium portions by repeated centrifuging (20000 g/20 minutes) at 0° C. Finally, the resulting liposomes are freeze-dried in the Multivial. Application is as a colloidal dispersion in 0.9 percent by weight of sodium chloride solution.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of performing an NMR diagnostic procedure in a patient in need of the same comprising administering to the patient an effective amount of an NMR diagnostic medium and then exposing the patient to an NMR measurement step to which the diagnostic medium is responsive thereby imaging at least a portion of the patient's body, wherein the diagnostic medium comprises a physiologically compatible salt of (a) an anion of a complexing acid and (b) at least one central ion of an element with an atomic number of 21 to 29, 42, 44 or 57 to 83 chelated therewith, wherein the salt is of the formula I or II

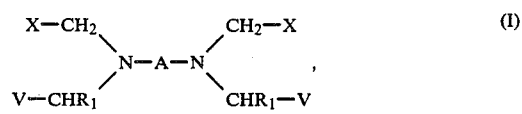

or $$N(CH_2X)_3, \quad (II)$$

wherein
X is —COOY, —PO$_3$HY or —CONHOY;
Y is a hydrogen atom, a metal ion equivalent or a physiologically biocompatible cation of an inorganic or organic base or amino acid;
A is —CHR$_2$—CHR$_3$—, —CH$_2$—CH$_2$—(ZCH$_2$—CH$_2$)$_m$—,

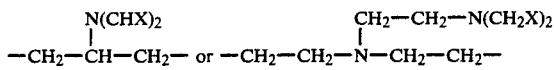

each R$_1$ is a hydrogen atom or methyl;
R$_2$ and R$_3$ together represent a trimethylene group or a tetramethylene group or individually are hydrogen, C$_{1-8}$-alkyl, phenyl or benzyl,
W is —NN—, —NHCOCH$_2$— or —NHCS—;
m is the number 1, 2 or 3
Z is an oxygen atom, a sulfur atom, >NCH$_2$X, or >NCH$_2$CH$_2$OR$_4$
R$_4$ is C$_{1-8}$-alkyl
V is one of the X groups or is —CH$_2$OH, or —CONH(CH$_2$)$_n$X,
n is a number from 1 to 12;
if R$_1$, R$_2$ and R$_3$ are hydrogen atoms, both V's together are the group

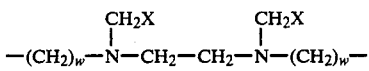

w is a number 1, 2 or 3;
provided that at least two of the substituents Y are metal ion equivalents of an element with an atomic number of 21 to 29, 42, 44 or 57 to 83.

2. A method of claim 1 wherein the concentration of salt in the medium is 1 μmole to 1 mole.

3. A method of claim 1 wherein the concentration of salt in the medium is 1 μmole to 5 mmole.

4. A method of claim 1 wherein the concentration of salt in the medium is 250 mmole to 1 mole.

5. A method of claim 1 wherein the salt in the medium is the monosodium/mono-N-methylglucamine mixed salt of the gadolinium(III) complex of diethylenetriaminepentaacetic acid.

6. A method of claim 1 wherein the salt in the medium is the disodium salt of the gadolinium(III) complex of diethylenetriaminepentaacetic acid.

7. A method of claim 1 wherein the salt in the medium is the di-N-methylglucamine salt of the iron(III) complex of diethylenetriaminepentaacetic acid.

8. A method of claim 1 wherein the salt in the medium is the disodium salt of the iron (III) complex of diethylenetriaminepentaacetic acid.

9. A method of claim 1 wherein the salt in the medium is the disodium salt of the manganese(II) complex of diethylenetriaminepentaacetic acid.

10. A method of claim 1 wherein the salt in the medium is the di-N-methylglucamine salt of the bismuth-(III) complex of diethylenetriaminepentaacetic acid.

11. A method of claim 1 wherein the salt in the medium is the di-N-methylglucamine salt of the manganese(II) complex of trans-1,2-cyclohexenediaminetetraacetic acid.

12. A method of claim 1 wherein the salt in the medium is the disodium salt of the ytterbium(III) complex of diethylenetriaminepentaacetic acid.

13. A method of claim 1 wherein the salt in the medium is the N-methylglucamine salt of the gadolinium-(III) complex of 1,4,7,10-tetraazacyclododecanetetraacetic acid.

14. A method of claim 1 wherein the salt in the medium is the disodium salt of the manganese(II) complex of trans-1,2-cyclohenediaminetetraacetic acid.

15. A method of claim 1 wherein the salt in the medium is the disodium salt of the bismuth(III) complex of diethylenetriaminepentaacetic acid.

16. A method of claim 1 wherein the salt in the medium is the di-N-methyglucamine salt of the gadolinium(III) complex of 13,23-dioxo-15,18,21-tris-(carboxymethyl)-12,15,18,21,24-pentaazapentatriacontanedioic acid.

17. A method of claim 1 wherein the salt in the medium is the sodium salt of the gadolinium(III) complex of 1,4,7,10-tetraazacyclododecanetetraacetic acid.

18. A method of claim 1 wherein the salt in the medium comprises liposomes charged with the gladolinium(III) complex of diethylenetriaminepentaacetic acid.

19. A method of claim 1 wherein the salt in the medium is the disodium salt of the holmium(III) complex of diethylenetriaminepentaacetic acid.

20. A method of claim 1 wherein the salt in the medium is the disodium salt of the lanthanum(III) complex of diethylenetriaminepentaacetic acid.

21. A method of claim 1 wherein the salt in the medium is the disodium salt of the di-N-methylglucamine salt of the ytterbium(III) complex of diethylenetriaminepentaacetic acid.

22. A method of claim 1 wherein the salt in the medium is the disodium salt of the sumarium(III) complex of diethylenetriaminepentaacetic acid.

23. A method of claim 1 wherein the salt in the medium is the disodium salt of the gadolinium(III) complex of 13,23-dioxo-15,18,21-tris-(carboxymethyl)-12,15,18,21,24-pentaazapentatriacontanedioic acid.

24. In a method of imaging body tissue in a patient, comprising subjecting the patient to NMR tomography, the improvement comprising, prior to performing the NMR tomography, administering to the patient an effective amount of a pharmaceutical agent for affecting the relaxation times of atoms in body tissues undergoing NMR diagnosis, whereby image contrast is enhanced, said agent comprising an amount, effective to affect such relaxation times, of a paramagnetic, physiologically compatible salt of a physiologically compatible chelate complex of an ion of a lanthanide element of atomic numbers 57–70, or of a transition metal of atomic numbers 21–29, 42, or 44; and a pharmaceutically acceptable carrier.

25. A method of claim 24 wherein the concentration of said salt in the agent is 1 μmole to 1 mole.

26. In a method of imaging body tissue in a patient, comprising subjecting the patient to NMR tomography, the improvement comprising, prior to performing the NMR tomography, administering to the patient an effective amount of a pharmaceutical agent for affecting the relaxation times of atoms in body tissues undergoing NMR diagnosis whereby image contrast is enhanced, said agent comprising an amount effective to affect such relaxation times of a paramagnetic, physiologically compatible salt of a complex of an ion and a ligand; and a pharmaceutically acceptable carrier;

wherein the complexed ion is an ion of a lanthanide element of atomic numbers 57-70, or of a transition metal of atomic numbers 21-29, 42, or 44;

and wherein the ligand is that of a complexing agent which (a) is an aminopolycarboxylic acid which is nitrilotriacetic acid, N-hydroxyethyl-N,N',N'-ethylenediaminetriacetic acid, N,N,N',N'',N''-diethylenetriaminepentaacetic acid or N-hydroxyethyliminodiacetic acid;

(b) of the formula

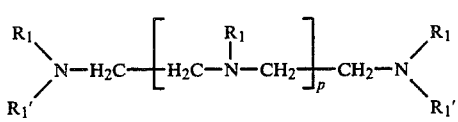

wherein $R_1$ and $R_1'$ are identical or different and each is hydrogen or alkyl of 1-4 carbon atoms and p is an integer of 0-4; or (c) an aminopolycarboxylic acid of the formula

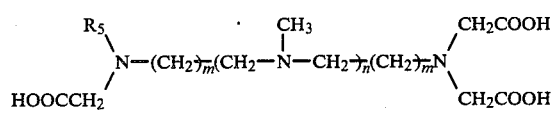

wherein
m is an integer of 1 to 4,
n is an integer of 0 to 2, and
$R_5$ is $C_{4-12}$-alkyl, $C_{4-12}$-alkenyl, $C_{4-12}$-cycloalkyl, $C_{4-12}$-cycloalkenyl, $C_{7-12}$-hydrocarbon aralkyl, $C_{8-12}$-hydrocarbon alkenyl, $C_{6-12}$-hydrocarbon aryl or —$CH_2COOH$.

27. A method of claim 26 wherein the administration is orally or intravasally and is performed about 15-60 minutes before performing the NMR tomography.

28. A method of claim 27 wherein the dosage of complex salt is 1-100 μmol/kg intravenously.

29. A method of claim 26, wherein the pharmaceutical agent has a pH of 6.5-7.5.

30. A method of claim 26, wherein the pharmaceutical agent is blood isotonic.

31. A method of claim 26, wherein the pharmaceutical agent comprises the paramagnetic complex salt dissolved or suspended in water in a concentration of 5-250 mmol/l.

32. A method of claim 26, wherein in the pharmaceutical agent, the complex salt is a salt of the complexed ion with an inorganic or organic acid or base.

33. A method of claim 26, wherein in the pharmaceutical agent, the inorganic or organic acid or base is hydrochloric acid, sulfuric acid, acetic acid, citric acid, aspartic acid, glutamic acid, sodium hydroxide, glucamine, N-methylglucamine, N,N-dimethylglucamine, ethanolamine, diethanolamine, morpholine, lysine, ornithine or arginine.

34. A method of claim 26, wherein in the pharmaceutical agent, the complexing agent is an aminopolycarboxylic acid which is nitrilotriacetic acid, N,N,N',N'-ethylenediaminetetraacetic acid, N-hydroxyethyl-N,N',N'-ethylenediaminetriacetic acid, N,N,N',N'',N''-diethylenetriaminepentaacetic acid or N-hydroxyethyliminodiacetic acid.

35. A method of claim 26, wherein in the pharmaceutical agent, the complexing agent is of the formula

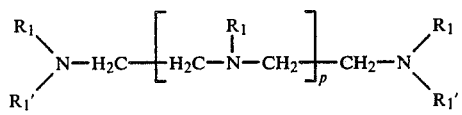

wherein $R_1$ and $R_1'$ are identical or different and each is hydrogen or alkyl of 1-4 carbon atoms and p is an integer of 0-4.

36. A method of claim 26, wherein in the pharmaceutical agent, the complexing agent is an aminopolycarboxylic acid of the formula

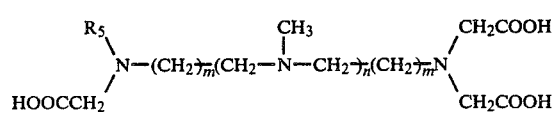

wherein
m is an integer of 1 to 4,
n is an integer of 0 to 2, and
$R_5$ is $C_{4-12}$-alkyl, $C_{4-12}$-alkenyl, $C_{4-12}$-cycloalkyl, $C_{4-12}$-cycloalkenyl, $C_{7-12}$-hydrocarbon aralkyl, $C_{8-12}$-hydrocarbon alkenyl, $C_{6-12}$-hydrocarbon aryl or —$CH_2COOH$.

37. A method of claim 26, wherein in the pharmaceutical agent, the complexed ion is an ion of a lanthanide element of atomic numbers 57-70.

38. A method of claim 26, wherein in the pharmaceutical agent, the complexed ion is an ion of a transition metal of atomic numbers 21-29, 42, or 44.

39. A method of claim 34, wherein in the pharmaceutical agent, the complexed ion is an ion of a lanthanide element of atomic numbers 57-70.

40. A method of claim 34, wherein in the pharmaceutical agent, the complexed ion is an ion of a transition metal of atomic numbers 21-29, 42, or 44.

41. A method of claim 35, wherein in the pharmaceutical agent, the complexed ion is an ion of a lanthanide element of atomic numbers 57-70.

42. A method of claim 35, wherein in the pharmaceutical agent, the complexed ion is an ion of a transition metal of atomic numbers 21-29, 42, or 44.

43. A method of claim 36, wherein in the pharmaceutical agent, the complexed ion is an ion of a lanthanide element of atomic numbers 57-70.

44. A method of claim 36, wherein in the pharmaceutical agent, the complexed ion is an ion of a transition metal of atomic numbers 21-29, 42, or 44.

45. A method of claim 26, wherein in the pharmaceutical agent, the paramagnetic complex salt is the di-N-methylglucamine salt of the manganese(II) complex of ethylenediaminetetraacetic acid.

46. A method of claim 26, wherein in the pharmaceutical agent, the paramagnetic complex salt is the N-methylglucamine salt of the gadolinium(III) complex of ethylenediaminetetraacetic acid.

47. A method of claim 26, wherein in the pharmaceutical agent, the paramagnetic complex salt is the di-N-methylglucamine salt of the gadolinium(III) complex of diethylenetriaminepentaacetic acid.

48. A method of claim 26, wherein in the pharmaceutical agent, the paramagnetic complex salt is the di-N-methylglucamine salt of the dysprosium(III) complex of diethylenetriaminepentaacetic acid.

49. A method of claim 26, wherein in the pharmaceutical agent, the paramagnetic complex salt is the di-N-methylgucamine salt of the holmium(III) complex of diethylenetriaminepentaacetic acid.

50. A method of claim 26, wherein in the pharmaceutical agent, the paramagnetic complex salt is the disodium salt of the manganese(II) complex of ethylenediaminetetraacetic acid.

51. A method of claim 26, wherein in the pharmaceutical agent, the paramagnetic complex salt is the complex ;ps
[Ni$_2$(C$_6$H$_{18}$N$_4$)$_3$]Cl$_4$.2H$_2$O.

52. A method of claim 26, wherein in the pharmaceutical agent, the paramagnetic complex salt is the N-methylglucamine salt of the gladolinium(III) complex of diethylenetriaminepentaacetic acid.

53. A method of claim 26, wherein in the pharmaceutical agent, the paramagnetic complex salt is the copper-(II) chloride complex of 4,7,13,16,21,24-hexaoxa-1,10-diazabicyclo[8.8.8]hexacosane.

54. A method of claim 26 wherein in the pharmaceutical agent, the paramagnetic complex salt is the N-methylglucamine salt of the iron(II) complex of ethane-1-hydroxy-1,1-diphosphonic acid.

55. A method of claim 26, wherein in the pharmaceutical agent, the paramagnetic complex salt is the di-lysine salt of the gadolinium(III) complex of diethylenetriaminepentaacetic acid.

56. A method of claim 26, wherein in the pharmaceutical agent, the paramagnetic complex salt is the dimorpholine salt of the manganese(II) complex of ethylenediaminetetraacetic acid.

57. A method of claim 26, wherein in the pharmaceutical agent, the paramagnetic complex salt is the tri-diethanolamine salt of the manganese(II) complex of diethylenetriaminepentaacetic acid.

58. A method of claim 26, wherein in the pharmaceutical agent, the paramagnetic complex salt is the tri-N-methylglucamine salt of the manganese(II) complex of diethylenetriaminepentaacetic acid.

59. A method of claim 26, wherein in the pharmaceutical agent, the paramagnetic complex salt is the N-methylglucamine salt of the dysprosium(III) complex of ethylenediaminetetraacetic acid.

60. A method of claim 26, wherein in the pharmaceutical agent, the complex ion is gadolinium(III).

61. A method of claim 60, wherein in the pharmaceutical agent, the ligand is N,N,N',N'',N''-diethylenetriaminepentaacetic acid.

62. A method of claim 61, wherein, in the pharmaceutical agent, the complex salt is a salt of the complexed ion with the cation of an inorganic base which is sodium or an organic base which is N-methylglucamine.

63. A method of claim 62, wherein in the pharmaceutical agent, said base is inorganic.

64. A method of claim 26, wherein in the pharmaceutical agent, the ligand is N,N,N',N'',N''-diethylenetriaminepentaacetic acid.

65. In a method of imaging body tissue in a patient, comprising subjecting the patient to NMR tomography, the improvement comprising, prior to performing the NMR tomography, administering to the patient an effective amount of a pharmaceutical agent for affecting the relaxation times of atoms in body tissues undergoing NMR diagnosis, whereby image contrast is enhanced, said agent comprising an amount, effective to affect such relaxation times, of a paramagnetic, physiologically compatible salt of a complex of an ion and, as a ligand, an acyclic or cyclic complexing agent containing organic nitrogen, phosphorus, oxygen or sulfur, the complexed ion being an ion of a lanthanide element of atomic numbers 57-70, or of a transition metal of atomic numbers 21-29, 42, or 44; and a pharmaceutically acceptable carrier.

66. The method of claim 65 wherein the salt is the di-N-methylglucamine salt of the nickel (II) complex of ethylenediaminetetraacetic acid.

67. A method of claim 65 wherein the salt is the diethanolamine salt of the cobalt (II) complex of ethylenediaminetetraacetic acid.

68. A method of claim 65 wherein the salt is the di-diethanolamine salt of the copper (II) complex of ethylenediaminetetraacetic acid.

* * * * *

UNITED STATES PATENT AND TRADEMARK OFFICE
CERTIFICATE OF CORRECTION

PATENT NO. : 4,647,447
DATED : March 3, 1987
INVENTOR(S) : Gries, et al

It is certified that error appears in the above-identified patent and that said Letters Patent is hereby corrected as shown below:

Column 29, lines 21-24: Cancel or delete Claim 54

Signed and Sealed this

Sixteenth Day of February, 1988

*Attest:*

DONALD J. QUIGG

*Attesting Officer*     *Commissioner of Patents and Trademarks*